(12) United States Patent
Koide

(10) Patent No.: US 8,715,742 B2
(45) Date of Patent: May 6, 2014

(54) METHOD FOR REDUCING WEIGHT IN A SUBJECT

(75) Inventor: Masafumi Koide, Aichi (JP)

(73) Assignee: BBK Bio Corporation, Tokyo (JP)

( * ) Notice: Subject to any disclaimer, the term of this patent is extended or adjusted under 35 U.S.C. 154(b) by 356 days.

(21) Appl. No.: 12/761,929

(22) Filed: Apr. 16, 2010

(65) Prior Publication Data

US 2010/0203176 A1 Aug. 12, 2010

Related U.S. Application Data

(63) Continuation of application No. 10/570,200, filed as application No. PCT/JP2004/012741 on Sep. 2, 2004, now abandoned.

(30) Foreign Application Priority Data

Sep. 2, 2003 (JP) .................................. 2003-309966

(51) Int. Cl.
  *A61K 35/60* (2006.01)
  *A61K 38/05* (2006.01)
  *A61K 48/00* (2006.01)
  *A01N 43/04* (2006.01)

(52) U.S. Cl.
  USPC .......... 424/523; 514/21.91; 514/44 R; 514/46

(58) Field of Classification Search
  None
  See application file for complete search history.

(56) References Cited

U.S. PATENT DOCUMENTS

| | | | |
|---|---|---|---|
| 4,414,238 A | | 11/1983 | Schmidl |
| 4,820,731 A | | 4/1989 | Mascioli et al. |
| 4,871,768 A | | 10/1989 | Bistrian et al. |
| 5,053,387 A | | 10/1991 | Alexander |
| 6,048,543 A | * | 4/2000 | Schneider et al. ............ 424/442 |
| 6,696,057 B1 | | 2/2004 | Bojrab |
| 7,179,491 B1 | | 2/2007 | Mag |
| 2004/0043013 A1 | * | 3/2004 | McCleary ..................... 424/94.1 |
| 2005/0238694 A1 | * | 10/2005 | Gerhardt et al. .............. 424/439 |

FOREIGN PATENT DOCUMENTS

| | | |
|---|---|---|
| DE | 20214827 | 2/2003 |
| EP | 0 367 724 | 5/1990 |
| EP | 0 567 433 | 4/1993 |
| EP | 0 674 902 | 2/1995 |
| EP | 0 855 181 | 7/1998 |
| EP | 1330957 | 7/2003 |
| JP | 5-252905 | 10/1993 |
| JP | 10-004918 | 1/1998 |
| JP | 10-139683 | 5/1998 |
| JP | 10-203972 | 8/1998 |
| JP | 11-501301 | 2/1999 |
| JP | 2001131575 A * | 5/2001 |
| JP | 2003-147388 | 5/2003 |
| WO | 96/25861 | 8/1996 |

OTHER PUBLICATIONS

Bullo-Bonet et al. Tumour necrosis factor, a key role in obesity?, Federation of European Biochemical Societies (FEBS) Letters 451 (1999) 215-219.*
Decision of Rejection — 2005-513667 — Jun. 15, 2010.
European Search Report—PCT/JP2004/012741—Dec. 16, 2010.

* cited by examiner

*Primary Examiner* — Michael G Hartley
*Assistant Examiner* — Nabila Ebrahim
(74) *Attorney, Agent, or Firm* — Young & Thompson

(57) ABSTRACT

A method is provided for reducing weight in a subject by administering an effective amount of a composition comprising omega-3 polyunsaturated fatty acid (PUFA), at least one of L-arginine, L-ornithine, an L-arginine precursor and an L-ornithine precursor, and at least one of a nucleobase, a nucleoside and a nucleic acid. The method can also be used to treat obesity, hyperlipidemia, diabetes and/or hypertension and for improving diathesis, or treating adult disease or disposition to adult disease.

10 Claims, 1 Drawing Sheet

| | |
|---|---|
| L-arginine (g) | 3.20 |
| ω-3 polyunsaturated fatty acid (g) | 1.00 |
| ω-6 polyunsaturated fatty acid (g) | 0.84 |
| Medium chain fatty acid (g) | 1.50 |
| Yeast RNA (g) | 0.32 |
| Carbohydrate (dextrin) (g) | 33.50 |
| Sodium (mg) | 275.00 |
| Potassium (mg) | 333.00 |
| Magnesium (mg) | 50.00 |
| Phosphorus (mg) | 133.00 |
| Chlorine (mg) | 300.00 |
| Iron (mg) | 2.00 |
| Copper (mg) | 0.30 |
| Manganese (mg) | 0.70 |
| Zinc (mg) | 1.70 |
| Iodine (mcg) | 25.00 |
| Selenium (mcg) | 8.30 |
| Chromium (mcg) | 5.00 |
| Molybdenum (mcg) | 4.20 |
| Vitamin A (mg) | 0.11 |
| Vitamin D (mcg) | 0.40 |
| Vitamin E (mg) | 1.67 |
| Vitamin K2 (mcg) | 9.20 |
| Vitamin B1 (mg) | 0.17 |
| Vitamin B2 (mg) | 0.18 |
| Niacin (mg) | 2.50 |
| Vitamin B6 (mg) | 0.25 |
| Vitamin B12 (mcg) | 0.40 |
| Vitamin C (mg) | 24.00 |
| Folic acid (mcg) | 33.30 |
| Pantothenic acid (mg) | 0.83 |
| Nitrogen source (g) | 14.00 |
| Fatty acid source (g) | 7.00 |

METHOD FOR REDUCING WEIGHT IN A SUBJECT

TECHNICAL FIELD

The present invention relates to a diet food having effects to reduce body weight and prevent/improve obesity and adult diseases, i.e., cardiovascular disorders, diabetes and hyperlipidemia, namely DIET.

BACKGROUND ART

Recently, there are increasing cases where diatheses of obesity, hyperlipemia, diabetes and hypertension are factors to affect or aggravate various diseases arising from a variety of circulatory or metabolic disorders. Specifically, although the human race originally has a genetic mechanism for coping with starvation (thrifty genes), the mechanism for coping with excessive food ingestion is merely a hypoglycemic action of insulin. However, recent problems in daily eating habits are excessive food ingestion and shortage in energy consumption, and there are demands for health care to prevent or improve obesity and arterial sclerosis, and hence, a variety of diet foods, supplements and alimentary therapies are now being earnestly studied.

On the other hand, a parenteral dietary supplement including a mixture of oils rich in ω-3 and ω-6 polyunsaturated fatty acids (PUFA) is recently disclosed. (For example, see Patent Literature 1: U.S. Pat. No. 4,820,731.) The invention described in Patent Literature 1 relates to a parenteral dietary supplement using ω-3 and ω-6 PUFA for minimizing risks of an infectious disease of a postoperative patient.

Also, a dietary supplement including ω-3 oils and middle-chain triglycerides (see, for example, Patent Literature 2: U.S. Pat. No. 4,871,768) and a composition for traumatic injury treatment including intact protein, arginine, carbohydrate and lipid including ω-3 fatty acids of fish oil and linoleic acid (see, for example, Patent Literature 3: U.S. Pat. No. 5,053,387) are also disclosed.

Furthermore, a technique related to a liquid elemental diet including carbohydrate, amino acid and lipid components having a pH ranging from approximately 3.0 to 4.4 is also disclosed (see, for example, Patent Literature 4: U.S. Pat. No. 4,414,238).

Problems to be Solved by the Invention

There is a problem that conventional simple caloric control using a supplement or alimentary therapy tends to cause a reaction of weight increase as a middle or long-term result, and a supplement added to a daily food cannot attain a sufficient effect in many cases.

Also, in conventional dieting using an extreme alimentary therapy or a special supplement, there is a case where essential nutrients for an adult cannot be sufficiently supplied, and not only a dieter feels hunger or malaise but also it is apprehended that the dieter's health is ruined.

Furthermore, since the dietary supplements described in the aforementioned Patent Literatures are devised for effective alimentation to improve the immunological function or to accelerate postoperative recovery, the quantity of supplied energy is set to be relatively excessive as compared with human energy consumption, and therefore, such dietary supplements cannot be used for diet for slimming.

In consideration of the present circumstances where an appropriate method for coping with worldwide increasing risks of obesity and adult diseases has not been established, the present invention was devised to create a novel diet food and dieting system through comprehensive examinations of clinical scientific metabolic theories, cellular biological knowledge and daily eating habits of present-day people.

The diet food herein means a food having various cosmetic effects including weight reduction, obesity improvement and slimming; a food for preventing and improving adult diseases (lifestyle-related illnesses) including obesity, hyperlipemia, diabetes and hypertension; a food for improving the diathesis of sport athletes; or a food capable of exhibiting an antagonistic action to prevent a diathesis of obesity, hyperlipemia, diabetes or hypertension from causing or becoming an aggravation factor of any of various circulatory, metabolic or neural system disorders.

An object of the invention is providing a diet food that is highly safe for human bodies and has a very effective function to metabolize body fat and utilize combustion energy.

Disclosure of the Invention

What is principally aimed at is that calorie generated by stimulating and activating a metabolizing process for body fat and carbohydrates is used for enhancing biosynthesis of cellular nucleic acid and proteins, and tissue/cellular physiological activities, so as to effectively accelerate combustion/consumption cycles.

For this purpose, nutrient sources to be supplied to a body are re-distributed in the composition of a diet food, so as to optimize a mechanism in which a dietary component functions as a catalyst-like factor for combusting endogenous fat and combustion energy immediately links at equilibrium with activation of a metabolic pathway, that is, an energy consumption system, from DNA replication and RNA synthesis to protein biosynthesis.

An effective and highly acceptable diet food for weight reduction, preventing obesity and adult diseases and its operation protocol devised based on the aforementioned novel idea not only exhibit remarkable effects in healthy people of middle and advanced age and people carrying adult diseases but also are effective for improving the diathesis of young people with fatness tendency without ruining their health.

The present inventor has referred to the metabolic pathways of an organism from different viewpoints, and has found that a diet including a combination of arginine, an ω-3 polyunsaturated fatty acid and nucleic acids has an effect to improve lipid combustion ability of organic tissues from a side different from the immunological function, an effect to activate the cellular metabolic function and an effect to improve the function of material synthesis systems for protein and the like from DNA replication and RNA synthesis to the protein synthesis through amino acid assembly, resulting in finding ideal diet food and dieting system.

When problems of efficacies in singly using respective amino acids, polyunsaturated fatty acids (PUFA) and nucleic acids included in the aforementioned diet and the effect of the combination of arginine, PUFA and nucleic acids attained in improvement of the immunological function are considered, a diet food or a dieting system from a novel viewpoint is introduced. Specifically, metabolic cycles exhibiting an interaction that cannot be attained in single use are rotated, resulting in a dieting effect useful for weight loss of fat people, conversion of body fat into muscle tissues and improvement or prevention of adult disease diatheses.

The present inventor has earnestly studied actions on body fat of amino acid components typified by L-arginine or L-ornithine, small peptides and PUFA, and has found a synergistic effect of a lipase activating action and a cell activity increasing action through secretion of growth hormone by these amino acid components and an α-amylase inhibitor action, a lipid metabolism improving action and an antiarteriosclerotic action of the ω-PUFA, resulting in devising a highly safe diet food with a very effective lipid metabolizing action.

The first invention is DIET including an ω-3 PUFA; and at least one of L-arginine, L-ornithine, an L-arginine precursor and an L-ornithine precursor.

The second invention is the diet food of the first invention further including an ω-6 PUFA.

The third invention is the diet food of the first invention in which whole or part of the ω-3 PUFA is included as fish oil.

The fourth invention is the diet food of the second invention in which whole or part of the ω-3 PUFA and the ω-6 PUFA are included as fish oil.

The fifth invention is the diet food of any of the first through fourth inventions in which an intake per meal of the diet food includes 0.1 g or more and 3.5 g or less of the ω-3 PUFA and 0.6 g or more and 15 g or less of the at least one of L-arginine, L-ornithine, an L-arginine precursor and an L-ornithine precursor.

The sixth invention is the diet food of any of the first through fifth inventions in which the fish oil is encapsulated.

The seventh invention is DIET including at least one of diacylglycerol, a medium or short chain fatty acid and a phytosterol and at least one of L-arginine, L-ornithine, an L-arginine precursor and an L-ornithine precursor.

The eighth invention is the diet food of any of the first through seventh inventions further including at least one of a nucleotide, a nucleoside and a nucleic acid.

The ninth invention is the diet food of the eighth invention in which the nucleo-base is at least one of adenine, guanine, hypoxanthine, xanthine, cytosine, uracil and thymine.

The tenth invention is the diet food of the eighth invention in which the nucleoside is at least one of uridine, adenosine, guanosine, cytidine, ribothymidine, deoxyadenosine, deoxyguanosine, deoxyuridine, deoxycytidine, thymidine, inosine and xanthosine.

The eleventh invention is the diet food of the eighth invention in which the nucleic acid is at least one of DNA, RNA and polynucleotide obtained by polymerizing nucleotides.

The twelfth invention is the diet food of the eighth invention in which an intake per meal of the diet food includes 0.1 g or more and 1.5 g or less of at least one of a nucleic acid, a nucleo-base and a nucleoside.

The thirteenth invention is the diet food of any of the first through twelfth inventions further including at least one of maltodextrin, cluster dextrin, indigestible dextrin and oligosaccharide.

The fourteenth invention is the diet food of any of the first through thirteenth inventions further including at least one of a mucopolysaccharide and a uronic acid-containing polysaccharide.

The fifteenth invention is the diet food of any of the first through fourteenth inventions further including a component having an absorption suppressing action for carbohydrates and lipid.

The sixteenth invention is the diet food of any of the first through fifteenth inventions which is included in a low-calorie food of an intake per meal of 400 Kcal or less.

The seventeenth invention is the diet food of any of the first through sixteenth inventions further including yoghurt or a probiotics material derived from yoghurt.

The eighteenth invention is the diet food of any of the first through seventeenth inventions further including a water-absorbing fiber component.

The nineteenth invention is the diet food of any of the first through eighteenth inventions further including at least one of an anorectic component, a circulatory stimulating component, a lipid decomposition/consumption accelerating component and an antioxidant component.

The twentieth invention is the diet food of any of the first through nineteenth inventions further including at least one of glutamine, branched chain amino acid, vitamin A, vitamin B complex, vitamin C, vitamin D complex, vitamin E, β-carotene, linolenic acid, triglyceride linolenate, eicosapentaenoic acid, triglyceride eicosapentaenate, docosahexaenoic acid and triglyceride docosahexaenate.

The twenty-first invention is the diet food of any of the first through twentieth inventions in which active ingredients are substances derived from natural products.

The twenty-second invention is the diet food of any of the first through twenty-first inventions for use for keeping health or improving a diathesis of a fat person, a person having an adult disease like atherosclerosis or metabolic disposition or a person affected by an adult disease.

The twenty-third invention is the diet food of any of the first through twenty-second inventions for use for keeping health or improving a diathesis of a domestic animal, a fowl or a pet.

The twenty-fourth invention is a diet food composition including (A) 0.1 through 6 wt % of at least one of L-arginine, L-ornithine, an L-arginine precursor and an L-ornithine precursor; (B) 0.02 through 1.2 wt % of ω-3 PUFA; and (C) 0.02 through 2 wt % of nucleic acid.

The twenty-fifth invention is a liquid diet food composition including (A) 0.1 through 6 wt % of at least one of L-arginine, L-ornithine, an L-arginine precursor and an L-ornithine precursor; (B) 0.02 through 1.2 wt % of ω-3 PUFA; (C) 0.02 through 2 wt % of nucleic acid; (D) 1 through 7 wt % of protein or peptide; (F) 1 through 10 wt % of carbohydrate; and (G) 0.5 through 5 wt % of lipid, in which water is used as a solvent.

The twenty-sixth invention is a liquid DIET composition including (A) 0.1 through 6 wt % of at least one of L-arginine, L-ornithine, an L-arginine precursor and an L-ornithine precursor; (B) 0.02 through 1.2 wt % of ω-3 PUFA; (C) 0.02 through 2 wt % of nucleic acid; (D) 1 through 7 wt % of protein or peptide; (E) 1 through 10 wt % of saccharide; (F) 0.5 through 5 wt % of lipid; (G) 0.01 through 2 wt % of ginger juice; and (H) 0.3 through 10 wt % of natural fruit juice or a fruit juice-like component, in which water is used as a solvent.

In more detail, the present invention is a diet food including an ω-3 PUFA and at least one of L-arginine, L-ornithine, an L-arginine precursor and an L-ornithine precursor.

First, among a large number of amino acids, the arginine is cationic and unique and is easily transferred into cells. Also, polyamine obtained by linking some arginines works as a vehicle capable of transporting an exotic molecule, which cannot singly enter a cell, into a cell. Furthermore, the arginine also exhibits actions to accelerate secretion of growth hormone and glucagon and to activate biological function of lipase.

Moreover, the ornithine has a function to complement the arginine action. Accordingly, it is occasionally taken as a supplement by an athlete such as a bodybuilder. However, the contents of the arginine and the ornithine in general food protein are small, and it is difficult to express the arginine specific action in a body by taking general food. Furthermore, when the arginine is simply ingested, neutral fat once decomposed into glycerol and fatty acid by lipase can be easily restored to the original form.

At this point, when an ω-3 PUFA, an ω-6 PUFA or exotic short or medium chain fatty acid is present, the neutral fat cannot be restored to the original form, and endogenous fatty acid cannot help entering a combustion metabolic pathway.

Also, when mono-glyceride or di-glyceride is present, a further higher effect can be attained. When nucleic acids are sufficiently supplied, combustion energy can be supplied to a material synthesis system, and hence, re-transformation to saccharide or fat can be prevented.

Specifically, it is devised to supply, as a diet food for reducing body weight or preventing/improving obesity and adult diseases, a food including an ω-3 PUFA, an ω-6 PUFA and a nucleic acid typified by ribonucleic acid as specific functional components.

As the theoretic ground, the arginine accelerates secretion of growth hormone and activates metabolism as well as activate biological function of lipase for fat decomposition and is an essential amino acid for synthesis of RNA and polyamine.

Also, the L-ornithine plays an effective role in effective expression of immunological functions and a liver function, and is related to synthesis and secretion of the growth hormone by a pituitary gland. Accordingly, it improves the cell metabolism and reduces fat, and hence is useful as a diet component. When the ornithine is combined with the arginine, the secretion of the growth hormone is more effectively accelerated.

On the other hand, with respect to the ω-3 PUFA or the ω-6 PUFA, arachidonic acid is a precursor of PG, eicosapentaenoic acid improves insulin action, and docosahexaenoic acid reduces low density lipoprotein and improves the activity of cerebral nerves. Also, the ω-3 or ω-6 PUFA is bonded to glycerin freed from neutral fat so as to prevent re-bonding of endogenous fatty acid and accelerate the decomposition of endogenous lipid.

Accordingly, hypertriglyceridaemia, that is, the basic diathesis of syndrome X and deadly quartet (hypertension, diabetes, hyperlipemia and obesity), can be improved. Also, in the same manner as in, for example, protein synthesis of cultured cells consuming calorie in a medium, nucleic acids including ribonucleic acid increase energy consumption required in intracellular metabolism in a process mainly from RNA assembly to protein synthesis. Energy generated through combustion of endogenous fatty acid inhibited from re-bonding to glycerin is effectively consumed in the process from the RNA assembly through recruit of amino acid to the synthesis of peptide and protein. Accordingly, excessive fat tissues are processed in the metabolic cycle, so as to exhibit a remarkable effect for weight loss and prevention of an adult disease. Furthermore, increase of protein included in muscles and the like leads to increase of basal metabolism, and hence, the dieting effect is further reinforced.

The present invention can be DIET including not only the ω-3 PUFA but also an ω-6 PUFA.

In the diet food of this invention, whole or part of the ω-3 PUFA and the ω-6 PUFA are preferably included as fish oil.

In the diet food of this invention, an intake per meal of the diet food includes 0.1 g or more and 3.5 g or less of the ω-3 PUFA and 0.6 g or more and 15 g or less of the at least one of L-arginine, L-ornithine, an L-arginine precursor and an L-ornithine precursor. In other words, an intake per day of the diet food includes 0.5 g or more and 10 g or less and preferably 0.6 g or more and 7 g or less of the ω-3 PUFA, and 2 g or more and 40 g or less of at least one of the L-arginine, the L-ornithine, the L-arginine precursor and the L-ornithine precursor.

In the diet food of the invention, the fish oil is encapsulated. The smell peculiar to fish oil tends to lower the intake motivation, and any of various means for reducing or eliminating smell and favoring with ginger juice or yoghurt as well as the encapsulation can be employed as an effective method for processing the smell of fish oil.

In one aspect of the invention, the diet food includes at least one of diacylglycerol, a medium or short chain fatty acid and a phytosterol and at least one of L-arginine, L-ornithine, an L-arginine precursor and an L-ornithine precursor.

In this invention, the diacylglycerol and the middle or short chain fatty acid have a fatness preventing action, a weight-increase suppressing action and the like. On the other hand, the phytosterol has a function to inhibit absorption of cholesterol in a process where cholesterol is dissolved in bile acid to be absorbed.

Accordingly, when either or both of them are ingested together with the arginine and ornithine, a synergistic action of the increase of the cell metabolism and the decomposition of the endogenous fat with the lipid metabolism improvement and the combustion can be attained, and since the used energy is thus increased, energy balance exceeds the critical point and is inclined to be negative, resulting in exhibiting the dieting effect. In this case, the ω-3 PUFA or the ω-6 PUFA may be used as a component of the lipid, or nucleic acid may be included in addition to the lipid, the arginine and the like so as to further enhance the dieting effect.

The diet food of this invention preferably includes a nucleic acid as purine substrate source.

Examples of the nucleic acid, purine substrate source, are natural nucleic acid substrates, nucleosides, nucleo-bases, RNA, DNA, equivalence of any of them, and/or a mixture including one or more of these compounds.

The nucleo-bases, the nucleosides and the nucleic acids are materials of an energy use system required in the intracellular metabolism in the process mainly from the RNA assembly through the DNA transcription to the protein synthesis, and in addition, they increase basal metabolism energy by the cell tissues as a middle-term result of the protein synthesis.

Accordingly, energy generated through combustion of the free fatty acid generated by activated lipase that derived from arginine is effectively consumed in the process from the RNA assembly through the recruit of amino acid to the synthesis of peptide and protein. In other words, the nucleo-bases, the nucleosides and the nucleic acids work to link the protein synthesis function to the fat metabolizing action of the diet food of this invention including at least one of the L-arginine, the L-ornithine, the L-arginine precursor and the L-ornithine precursor, so as to bring the consumption and the effective use of excessive energy.

On the other hand, the nucleo-base is preferably at least one of adenine, guacine, hypoxanthine, xanthine, cytosine, uracil and thymine.

The nucleoside is preferably at least one of uridine, adenosine, guanosine, cytidine, ribothymidine, deoxyadenosine, deoxyguanosine, deoxyuridine, deoxycytidine, thymidine, inosine and xanthosine.

The nucleic acid is preferably at least one of DNA, RNA and polynucleotide obtained by polymerizing nucleotides.

Furthermore, in the case where the nucleic acid substrate source is in a form of a free nucleic acid substrate, uracil is preferably included. Natural nucleotides include phosphate esters of natural nucleosides, for example, monophosphate esters such as adenylate (AMP), guanilate (GMP), uridilate (UMP), cytidilate (CMP), deoxythymidilate (dTMP) and deoxycytidilate (dCMP), and diphosphate esters or triphosphate esters of natural nucleoside such as ADP and ATP.

As a purified nucleic acid substrate source, baker's or brewer's yeast RNA or fish sperm and egg DNA is preferred, and any of the other biological materials may be used as a starting source.

With respect to a dose of the nucleic acid substrate source, in the case where a dieter is an adult, when the diet food of this invention is prepared so as to attain a dose per day of the RNA or an equivalent weight of another nucleic acid substrate source of 0.2 through 4.0 g, preferably 0.3 through 3 g and most preferably 0.5 through 2 g, a response of effective salvage nucleic acid synthesis can be easily obtained.

In other words, in one aspect of the invention, an intake per meal of the diet food includes 0.1 g or more and 1.5 g or less of at least one of a nucleic acid, a nucleobase and a nucleoside.

In consideration of the entire description above, when the appropriately mixed specific functional components including the arginine, the ω-3 PUFA, the ω-6 PUFA and the nucleic acids such as the ribonucleic acid are combined or replaced with meals mainly including general three essential nutrients of protein, lipid and carbohydrate, the diet food that functions independently of intake calorie and exhibits the effects to reduce the weight and prevent an adult disease can be obtained. Other amino acids such as lysine, proline, leucine, isoleucine and valine may be recruited or diacylglycerol, phytosterol and medium or short chain fatty acid may be combined in addition to or in place of the ω-3 or ω-6 PUFA.

In this invention, the diet food may further include at least one of maltodextrin, cluster dextrin and indigestible dextrin.

The maltodextrin, the cluster dextrin and the non-digestive dextrin obtained by processing starch with an enzyme or the like has an appropriate characteristic to ideally set the quantity of energy, the absorbing system, the taste and the like as a diet carbohydrate. In the case where glucose or sugar is simply ingested, the blood sugar is abruptly increased so as to accelerate the insulin secretion, various metabolic pathways such as protein kinase C, PI3 kinase and NO production are activated, and hence, angiopathy, obesity or an adult disease diathesis is aggravated as a medium or long-term result.

The maltodextrin, the cluster dextrin and the indigestible dextrin exhibiting characteristic digestive, absorption and metabolic patterns belong to a saccharide group capable of moderately increasing the blood sugar and planning to transfer to and use in a human body as carbohydrate. Accordingly, when the mixing ratio of the maltodextrin, the cluster dextrin or the indigestible dextrin in the present diet food is determined, a caloric intake and a dieting effect suitable for the aim can be realized.

Also, for adjusting the taste and the eating comfortableness, another natural or synthetic saccharide such as granulated sugar, sugar, trehalose or Aspartame is preferably included.

In this invention, the diet food may further include a mucopolysaccharide or a uronic acid.

The uronic acid-containing polysaccharide such as pectin, carageenan or alginic acid is a polymer that extracts moisture so as to provide a satiety feeling as food, and at the same time, has low calorie and exhibits a good performance to suppress the absorption of saccharide.

Also, hyaluronic acid provides protection and smoothness to skins and synovial tissues. Accordingly, the mixture of uronic acid in the diet food of this invention can be effective means for improving these effects. Natural materials including a large amount of uronic acid-containing polysaccharide or mucopolysaccharide, such as apples, seaweeds and yams, may be processed to be mixed.

In the present invention, the diet food may further include a component having an absorption suppressing action for saccharide and lipid.

Diet pills using a large number of natural or synthetic substances, such as yohimbine for inhibiting decomposition of fat, a compound having an absorption inhibiting action and an α-glycosidase inhibitor having a carbohydrate absorption inhibiting action, have been proposed, and a conventional type of lipid or saccharide absorption metabolism suppressing diet including *Aralia elata* of Alariaceae, gymnema extract, chitin chitosan, galcinia, polyphenol, catechin and the like used together is useful for reinforcing the performance of the diet food of this invention. Also, a component having an antioxidant action such as polyphenol is more preferably included.

In the present invention, the diet food may be included in a low-calorie food of an intake per meal of 400 Kcal or less, namely, a low-calorie food of an intake per day of 1200 Kcal or less.

The alimentary therapy for obesity through energy intake control is generally classified into a low-energy food of 1000 through 1300 Kcal, a maintenance food of 1600 through 1800 Kcal and a protein keeping/adjusting food, namely, a very low-energy food of approximately 600 Kcal in which carbohydrate and lipid are extremely reduced.

In order to attain a higher dieting effect, practice of calorie intake control combined with the diet food of the first invention, DIET, or the like is useful. Assuming that the basal metabolism is 24 Kcal/Kg and the kinetic energy is 300 through 500 Kcal, the maintenance energy is 1740 Kcal when the weight is 60 Kg, and a food with lower calorie is a relatively low-energy food.

Therefore, when three meals are composed of the diet food of the first invention taken twice a day with 500 Kcal in total and a calorie-control food of 700 through 800 Kcal taken once, the combustion energy obtained by accelerating the endogenous lipid decomposition with the merit of exogenous energy supply control is efficiently used in the protein synthesis process. Accordingly, the present invention can systematize the diet food/system capable of attaining highly effective combustion/elimination of fat tissues. In particular, differently from diet through simple calorie control and absorption inhibition, the present diet food can up regulate the energy generation, the cellular activity, the RNA synthesis and the protein synthesis even under high calorie control, and therefore, the physical strength and the health can be kept even during the dieting period.

In the present invention, the diet food may further include yoghurt or a probiotics material derived from yoghurt.

The probiotics, that is, "living microbes with properties useful for the health of humans", is useful for improving the enteral flora and maintaining the body functions healthy. Polyamines, that is, the product of yoghurt or yoghurt bacteria corresponding to typical probiotics, are known to accelerate cell protein synthesis and to have breeding activity. In other words, the yoghurt or lactic acid bacteria is a principal element as a material or a producer for producing, in the bowels, a substance useful for the human body activity.

Accordingly, the combination of the diet food of any of Claims 1 through 18 with yoghurt directly leads to useful means for continuously employing the diet food or system while maintaining the body functions with the action of the polyamines using the probiotics. In this case, the yoghurt or the lactic acid bacteria may be singly ingested separately from the diet food of any of Claims 1 through 18 or may be prepared to be ingested simultaneously with another diet food.

In the present invention, the diet food may further include a water-absorbing fiber component.

The water-absorbing fiber is known to swell within alimentary canals to provide satiety. Accordingly, when the diet food is combined with mannnan, guar gum, xanthan gum or inulin, physical and psychological satiety is attained through hydrated swell within the gastrointestinal tract so as to suppress excessive appetite, and therefore, continuous acceptability against the diet food can be attained.

Also, such a substance is expected to exhibit an action to reduce absorption of dietary components such as lipid and carbohydrate. Insoluble fiber such as cellulose, hemicellulose, lignin and agar may be used for modifying the eating comfortableness.

In the present invention, the diet food may further include at least one of an anorectic component, a circulatory stimulating component, a lipid decomposition/consumption accelerating component and an antioxidant component.

An agent for inhibiting uptake of serotonin, such as fluoxetine, is attracting attention. In a large number of drugs and natural products, there are substances having an appetite suppressing effect such as peptide for reducing appetite, compounds or derivatives of carbohydrates typified by morphine for suppressing gastric movement, and mazindol, fluvoxamine and the like. Substances affecting systems?? such as leptin and adiponectin can be useful materials.

On the other hand, capsaicin, raspberry ketone, carnitine, lycopene, taurine, saponin and xanthines have a fat decomposition/consumption accelerating action for stimulating the general circulation and decomposing/combusting the body fat. Also, the antioxidant component such as polyphenol and sesamin have an action to prevent arterial sclerosis.

In the present invention, the diet food may further include at least one of glutamine, branched chain amino acid, vitamin A, vitamin B complex, vitamin C, vitamin D complex, vitamin E, β-carotene, linolenic acid, eicosapentaenoic acid, docosahexaenoic acid, triglyceride linolenate, triglyceride eicosapentaenate and triglyceride docosahexaenate.

Furthermore, examples of the vitamins to be preferably included in the composition of the invention are vitamin A, vitamin E, vitamin C, vitamin D, vitamin K, folic acid, thiamine, riboflavine, vitamin B6, vitamin B12, niacin, biotin and pantothenic acid all in a pharmacologically allowable form.

Moreover, examples of mineral elements or minor elements to be preferably included in the composition of the invention are sodium, potassium, calcium, phosphorus, magnesium, manganese, copper, zinc, iron, selenium, chromium and molybdenum all in a pharmacologically allowable form.

In particular, the composition of the invention preferably includes beta-carotene (vitamin A), vitamin E, vitamin C, thiamine, vitamin B12, selenium chloride and zinc all in a pharmacologically allowable form.

In the present invention, active ingredients of the diet food are preferably substances substantially derived from natural products.

The present invention can be used for keeping health of or improving a diathesis of a fat person, a person having an adult disease (lifestyle-related illnesses) disposition or a person affected by an adult disease.

Furthermore, the present invention can be used for keeping health or improving a diathesis of a domestic animal, a fowl or a pet.

For improving the taste or flavor of the diet food of this invention, fruit juice of seakuwaser or the like or ginger juice is useful.

The concentrations of the active ingredients in providing the food of the invention as a drink are determined in consideration of the drinking comfortableness, the taste and the flavor, and the following diet drink compositions are preferred:

The first diet drink composition includes (A) 0.1 through 6 wt % of at least one of L-arginine, L-ornithine, an L-arginine precursor and an L-ornithine precursor; (B) 0.02 through 1.2 wt % of ω-3 PUFA; and (C) 0.02 through 2 wt % of nucleic acid.

Another liquid diet food composition includes (A) 0.1 through 6 wt % of at least one of L-arginine, L-ornithine, an L-arginine precursor and an L-ornithine precursor; (B) 0.02 through 1.2 wt % of ω-3 PUFA; (C) 0.02 through 2 wt % of nucleic acid; (D) 1 through 7 wt % of protein or peptide; (F) 1 through 10 wt % of carbohydrate; and (G) 0.5 through 5 wt % of lipid, in which water is used as a solvent.

Another liquid diet food composition includes (A) 0.1 through 6 wt % of at least one of L-arginine, L-ornithine, an L-arginine precursor and an L-ornithine precursor; (B) 0.02 through 1.2 wt % of ω-3 PUFA; (C) 0.02 through 2 wt % of nucleic acid; (D) 1 through 7 wt % of protein or peptide; (E) 1 through 10 wt % of carbohydrate; (F) 0.5 through 5 wt % of lipid; (G) 0.01 through 2 wt % of ginger juice; and (H) 0.3 through 10 wt % of natural fruit juice or a fruit juice-like component, in which water is used as a solvent.

Functions

In the present invention, the L-arginine has not only an action to accelerate the secretion of the growth hormone for activating metabolism but also an action to improve the activity of lipase, that is, a lipolytic enzyme. The lipase improved in the activity by the L-arginine efficiently hydrolyses triglyceride stored in blood and fat cells in a body so as to release fatty acid from glycerin. On the other hand, the L-ornithine affects the synthesis and the release of the growth hormone by the hypophysis. Accordingly, when the L-ornithine is ingested, the synthesis and the release of the growth hormone is activated, the metabolism of somatic cells is improved, and material synthesis is accelerated, resulting in accelerating the decomposition/consumption of body fat.

Furthermore, eicosapentaenoic acid and docosahexaenoic acid, that is, the ω-3 PUFA, are synthesized from linolenic acid in a very small amount, and the amount of arachidonic acid, that is, essential ω-6 PUFA, produced within a body is insufficient. The ω-3 PUFA or the ω-6 PUFA is bonded to glycerin freed from neutral fat within the body of a taker. Thus, the ω-3 PUFA or the ω-6 PUFA inhibits glycerin and endogenous fatty acid changing into triglyceride and VLDL again, so as to accelerate VLDL turnover in the blood plasma.

As a result, the VLDL is inhibited from being transferred to and stored in fat cells or arterial sclerosis nests. Accordingly, it is suitable as an acceptor of triglyceride decomposed by the arginine. Furthermore, the eicosapentaenoic acid is changed into thromboxane A3 and prevents a thrombotic disease, the docosahexaenoic acid improves the function of a nervous system, and both the acids suppress the expression of an adult disease disposition.

The ω-3 PUFA and the ω-6 PUFA included in the diet food are included in fish oil in a comparatively high ratio. The fish oil is comparatively inexpensive and is easily available, and hence is suitably added to the diet food of this invention.

In the present invention, when the fish oil included in the diet food is processed to reduce or eliminate the smell by, for example, encapsulation, the smell peculiar to the fish oil can be sealed and degradation of the fish oil through oxidation can be suppressed.

In the present invention, when diacylglycerol, phytosterol and middle or short chain fatty acid is used in addition to or in place of part of the ω-3 PUFA or ω-6 PUFA, the re-synthesis of body fat can be further suppressed. Specifically, the diacylglycerol in which two molecules of fatty acid are bonded to one molecule of glycerin is minimally re-synthesized into body fat after being absorbed into the body. Medium or short chain fatty acids having a carbon number of 8 through 10 have a higher water-soluble property than a general long or short chain fatty acid and are easily metabolized in cells. Furthermore, since the phytosterol has a property to dissolve in bile acid, it works to reduce the absorption of cholesterol.

When the arginine or the ornithine is ingested, the secretion of the growth hormone and the activation of the lipase are induced and the triglyceride is decomposed. Furthermore, dietary triglyceride is decomposed into fatty acid and glycerin and absorbed to be mixedly present with endogenous glycerin and fatty acid.

However, this decomposition process is reversible, and therefore, the fatty acids easily re-construct neutral fat together with glycerin and are disadvantageously difficult to combust/consume. When dietary diacylglycerol is combined, the neutral fat is minimally re-constructed, and the effect to combust the endogenous fatty acid is exhibited. Accordingly, owing to the presence of the diacylglycerol, the cellular stimulation and the lipase activation attained by the arginine are effectively linked with the combustion of fat and the increase of cellular metabolism. At this point, a balanced mixture of fatty acids including the ω-3 PUFA or the ω-6 PUFA is preferably exogenously supplied.

Also, a lipid group classified into cholesterol and neutral fat forms a large micelle in a blood through conjugation with apoprotein, and hence, reduction of the triglyceride is easily complemented by cholesterol. At this point, the phytosterol constructs a complex with bile acid in competition with internal cholesterol so as to enter enterohepatic circulation, but since the phytosterol is not absorbed into the body, they can suppress the absorption of the cholesterol and hence can adjust the expression level and the pattern of the apoprotein. Accordingly, when the diacylglycerol and the phytosterol are ingested in combination with the arginine and the ornithine, the obesity and the adult disease diathesis can be improved through the re-construction of the endogenous lipid and the change of the expression level of the apoprotein.

On the other hand, in the case where the endogenous lipid is preparedly adjusted by ingesting the diacylglycerol and the phytosterol, energy supply required for facilitating the cells and tissues, and body functions in the end, through the activation of the cellular metabolism attained by the arginine action is prepared, and processes for generating various functional materials are smoothly proceeded, resulting in up-regulating the basal metabolism through the increase in the tissue/cellular energetic consumption.

In the present invention, the nucleo-base, the nucleoside and the nucleic acid have the action to promote the energy consumption required in the intracellular metabolism in the process mainly from the RNA assembly to the protein synthesis. Accordingly, energy generated through the combustion of the free fatty acid inhibited from re-bonding to glycerin is effectively consumed in the process from the RNA assembly through the recruit of amino acid to the synthesis of peptide and protein.

In brief, the arginine, the ω-3 PUFA and the ω-6 PUFA, and the nucleobase, the nucleoside or the nucleic acid together construct diet food components ideal for a obesity or a person having an adult disease disposition.

The maltodextrin, the cluster dextrin or the indigestible dextrin included in the diet food of the present invention can supplement energy of the diet food in an idealistic manner. Specifically, when such dextrin is ingested, the blood sugar level is more moderately elevated than when glucose, sucrose or fructose is ingested. Therefore, the secretion of insulin into the blood is suppressed, and the downstream metabolism pathways are not excessively activated, resulting in suppressing the advancement of arterial sclerosis, lipid metabolism degradation or obesity stimulation derived from high insulin. Accordingly, a taker of the present diet food is free from abrupt hunger or fatigue.

In this invention, examples of the mucopolysaccharide included in the diet food are chondroitin sulfate, hyaluronic acid, heparin, keratan sulfate and dermatan sulfate, and although the mucopolysaccharide is a substance sufficiently produced in a body during a human growth period, the de novo production is reduced with ages, and hence it is significant to positively include it in a diet food. Such a mucopolysaccharide is a sticky viscous substance and is included in joints, eye balls, mucous membranes, blood vessel walls and the like to provide flexibility and smoothness of the tissues. Accordingly, appropriate supply of the mucopolysaccharide is useful for keeping blood vessels and skins flexible and suppressing advance of an adult disease disposition of arterial sclerosis.

When any of conventional type of lipid or saccharide absorption metabolism suppressing diet materials including a large number of natural or synthetic substances, such as yohimbine for inhibiting decomposition of fat, a compound having an absorption inhibiting function and an α-glycosidase inhibitor having carbohydrate absorption inhibiting action, and more specifically, Aralia elata of Alariaceae, gymnema extract, chitin chitosan, galcinia, polyphenol, catechin and the like or any of various porous materials such as cholestyramine or activated carbon is used together with the present diet food as a component having a saccharide or lipid absorption suppressing action included in the diet food, it is useful for reinforcing the performance of the diet food and the dieting system of this invention.

Furthermore, a polyphenol also has an antioxidant action, the death rate of cardiac diseases of French people is the lowest in Europe because they ingest a large amount of polyphenol included in red wine, and green tea includes polyphenols such as tannin, catechin and flavonoid. In the present diet, components having an absorption inhibiting function are preferably added as various natural material extracts.

When the diet food of this invention is combined with a general low-calorie food to provide calorie control per day of 1200 Kcal or less, the dietary energy supply can be suppressed. Specifically, assuming that the basal metabolism of an adult is approximately 24 Kcal/Kg and the kinetic energy is 300 through 500 Kcal, the maintenance energy necessary for an adult with a weight of 60 Kg is approximately 1740 Kcal.

In order to attain a higher dieting effect by using the diet food of this invention, it is appropriate to apply a protein keeping/adjusting food, namely, a very low-energy food in which saccharide and lipid are extremely reduced. When three meals are composed of the diet food of this invention taken twice a day with 500 Kcal in total and a calorie-controlled food of 500 Kcal or less taken once, the endogenous lipid decomposition is accelerated with the merit of exogenous energy supply control adjusted to 1000 Kcal or less.

The thus obtained lipid combustion energy is used in the protein synthesis process, and hence, the diet food can attain highly effective combustion/elimination of fat tissues. In particular, differently from diet through simple calorie control and absorption inhibition, the present diet food can improve the energy generation, the cellular activity, the RNA synthesis and the protein synthesis even under high calorie control, and therefore, the physical strength and the health can be maintained even during the dieting period.

In the present invention, the yoghurt or the probiotics material derived from yoghurt included in the diet food is useful for keeping the health of a person practicing slimming by using the diet food. The probiotics material means living microbes with properties useful for the health of humans, and polyamines, that is, the product of the probiotics material, are known to accelerate cell protein synthesis and to have breeding activity. Owing to the action of the polyamines, the dieting can be continued while keeping the body functions.

In the present invention, the water-absorbing fiber component included in the diet food can swell within bowels after being ingested, so as to provide satiety. Also, the water-absorbing fiber component exhibits a lipid or saccharide absorption reducing action.

In the present invention, the anorectic component included in the diet food has an action to inhibit uptake of serotonin like fluoxetine. Owing to this action, the intestinal movement of the taker is suppressed so as to reduce the appetite for practicing effective dieting. Also, an alkaloid or its derivative working on the central nervous system for reducing the appetite can be included.

In the present invention, the glutamine, the vitamin A, the vitamin B complex, the vitamin C, the vitamin D complex, the vitamin E, the β-carotene, the linolenic acid, the triglyceride linolenate, the triglyceride eicosapentaenate, the triglyceride docosahexaenate or the like included in the diet food assists the dieting effect as well as are useful for keeping the health of the taker through the supplement of essential nutrients during the dieting period.

In the present invention, the active ingredients of the diet food are preferably substances substantially derived from natural products.

The present invention can be used for keeping health of or improving diathesis of a fat person, an athlete, a person having an adult disease disposition or a person affected by an adult disease, so as to attain remarkable effects.

Furthermore, when the diet food of the invention is used for domestic animals and fowls such as cows, pigs and chickens, and pets such as dogs and cats, the effects to keep health or improve diatheses of such animals can be exhibited in the same manner as in the case where it is ingested by a human.

Also, when the eating comfortableness is improved by fruit juice or a flavor, the attachment of the taker for the diet food can be usefully improved.

EFFECTS OF THE INVENTION

According to the present invention, body fat can be safely and effectively reduced by ingesting the diet food, so as to effectively prevent or improve an adult disease disposition such as obesity, diabetes or hyperlipidemia.

BRIEF DESCRIPTION OF DRAWINGS

FIG. 1 is a component table of exemplified components of a diet food.

BEST MODE FOR CARRYING OUT THE INVENTION

Now, preferred embodiments of the invention will be described in detail.

The present invention provides a diet food including a mixture of PUFA and L-arginine or the like in an effective aggregation amount for prevention and improvement of adult diseases and improvement of obesity.

In general, fatty acid freed in a body is incorporated into mitochondria present in cells, changed into a form easily usable as energy with aerobically generating ATP through β-oxidation, TCA cycles and oxidative phosphorylation, and decomposed into carbon dioxide and water. Accordingly, it is a significant basic strategy for improvement of obesity and a dieting system to proceed decomposition and combustion of lipid.

Specifically, although the principal points of a conventional dieting system are absorption control of caloric food and energy supply reduction through food reduction, the principal point of the present diet is acceleration of material metabolic cycle by paying attention to the decomposition and combustion of lipid. Therefore, as characteristics of the dieting system using the diet food of this invention, body fat can be effectively reduced and a symptom such as fatigue or malaise derived from energy shortage minimally occurs.

The diet food of this invention is ingested by a fat person or a patient of a adult disease for preventing and improving adult diseases and preventing and improving obesity, or is dosed to a precritical person with an adult disease disposition.

Embodiment 1

The diet food of this invention includes a mixture of an ω-3 PUFA and at least one of L-arginine, L-ornithine, an L-arginine precursor and an L-ornithine precursor.

The ω-3 PUFA of this embodiment may be in a form of free acid or a form suitable for physiological supply of the ω-3 PUFA such as a form of triglyceride. Particularly preferable examples of the ω-3 PUFA of this embodiment are eicosapentaenoic acid (hereinafter sometimes referred to as "EPA") and docosahexaenoic acid (hereinafter sometimes referred to as "DHA"). Such an ω-3 PUFA is included in a comparatively high ratio in linseed oil or fish oil such as menhaden oil, salmon oil, mackerel oil, cod liver oil or anchovy oil.

The L-arginine precursor or the L-ornithine precursor of this embodiment includes small peptide rich in L-arginine or L-ornithine, respectively. Also, the L-arginine or the L-ornithine may be in a free form or a salt together with, for example, phosphoric acid, citric acid, tartaric acid, formic acid, adipic acid or lactic acid.

The diet food of this embodiment may be a supplement composed of merely the mixture of the ω-3 PUFA and the L-arginine or the like and is generally added to general food. As the form of the supplement, any of the forms of generally commercially available products such as a drink, a solid matter, a capsule, a tablet and granules can be employed.

On the other hand, in the case where the diet food is prepared with general food, the aforementioned components prepared in the form of a liquid, a solid matter, a semi-solid matter including a jelly, a mixture of a liquid and a jelly-like substance or granules are added to food for use. Applicable foods are confections such as baked wafers, crackers, biscuits, cookies and cakes, breads such as a loaf, a bun, a roll, a Danish pastry, a crescent and a stick-shaped bread, cereals, noodles, chocolates, candies, tablets, cold sweets such as ice creams and sherbets, Japanese confections such as a bun or a rice cake with bean jam filling, and pates.

Also, vegetable fiber, an olive leaf, an olive leaf extractable matter, luteolin or a luteolin derivative may be added. Owing to the action of the olive leaf, the olive leaf extractable matter, the luteolin or the luteolin derivative to suppress the increase of a blood sugar level, since the decomposition of nutrients (such as starch and amylose) is inhibited by an amylase inhibiting action in an organism, generation of glucose easily absorbed by the organism is suppressed, so as to suppress the increase of the blood sugar level.

Furthermore, a compound including a variety of diet materials such as salacia reticulate, chitosan, mulberry, aloe and plantain may be an additional component, and vitamins and various minerals may be added thereto. Examples of the vitamins are vitamin A, vitamin B1, vitamin B2, vitamin B6, vitamin D and vitamin E. Furthermore, creatine, citric acid, calcium and iron can be added.

With respect to an intake of the diet food of this embodiment, the amount of the ω-3 PUFA generally supplied to an adult over a treatment period is preferably 2.0 g or more per day. Also, the amount of the L-arginine, the L-ornithine or the mixture of them supplied over the treatment period is preferably 10 g or more per day.

The diet food or the supplement is administered preferably for 15 days or more, for example, over 15 through 60 days and once through four times a day. For further keeping the diathesis improving effect, the present diet food is expected to be ingested once or twice a day over a long period of time.

Accordingly, the amount of the ω-3 PUFA included in the diet food ingested per day is preferably not less than 0.5 g and not more than 10 g, and the amount of the L-arginine, the L-ornithine or the mixture of them is preferably not less than 2 g and not more than 40 g. In other words, as an intake per meal, the amount of the ω-3 PUFA is preferably not less than 0.1 g and not more than 3.5 g, and the amount of at least one of the L-arginine, the L-ornithine, the L-arginine precursor and the L-ornithine precursor is preferably not less than 0.6 g and not more than 15 g.

However, the amounts of the ω-3 PUFA and the L-arginine, the L-ornithine or the mixture of them to be supplied per day for attaining a desired effect can be varied depending upon the treatment period (days) and individual factors of a patient or the like to be treated.

The ω-3 PUFA is preferably included in the form of fish oil. In this case, when the pH is adjusted to approximately 3 through 4 by an edible acid, the smell peculiar to the fish oil can be reduced. Also, when the fish oil is encapsulated, the smell can be sealed and degradation of the fish oil through oxidation can be suppressed so as to improve the storage property.

When the L-arginine or the L-arginine precursor is added in this embodiment, the L-arginine or the like has not only an action to accelerate secretion of the growth hormone for activating metabolism but also a function to activate the lipase, that is, a lipolytic enzyme. The lipase activated by the L-arginine efficiently hydrolyses triglyceride stored in fat cells within the body so as to free fatty acid and glycerin. The fatty acid and glycerin thus freed are reused for protein synthesis in the cells or consumed through combustion as an energy source depending upon the tissue, intracellular or extracellular physiological environments.

On the other hand, when the L-ornithine or the L-ornithine precursor is added in this embodiment, the L-ornithine or the like affects the pituitary gland of the taker so as to activate the synthesis and the release of the growth hormone and improve the metabolism of somatic cells, resulting in accelerating the decomposition and the consumption of body fat.

Also, the L-arginine has an action to remove ammonia within the body and the L-ornithine has an action to complement this action. Accordingly, even if intravital metabolisms are inclined to tissue disorganization due to undernutrition or strain, a detoxication action can be exhibited.

Furthermore, the ω-3 PUFA included in the diet food of this embodiment is bonded to the glycerin freed from endogenous triglyceride within the body of the taker. Thus, the ω-3 PUFA prevents endogenous fatty acid from converted into triglyceride again to be stored in fat tissues.

As a result, the diet food of this embodiment effectively reduces body fat of the taker through the synergistic effect of the ω-3 PUFA and the L-arginine or the L-ornithine, so as to prevent/improve adult diseases and obesity.

Embodiment 2

A diet food of this embodiment includes a mixture of ω-6 PUFA and at least one of L-arginine, L-ornithine, an L-arginine precursor and an L-ornithine precursor.

The ω-6 PUFA of this embodiment may be in a form of free acid or in a form of triglyceride suitable for physiological supply of the ω-6 PUFA.

Particularly preferable examples of the ω-6 PUFA of this embodiment are linolenic acid and arachidonic acid, and linolenic acid is the most preferred. The preferable ω-6 PUFA is included in a comparatively high ratio in vegetable oil such as safflower oil, sunflower oil, soybean oil, cotton seed oil or corn oil.

Also the diet food of this embodiment is administered to a taker in the form of a supplement or in the form where it is added to general food as in the aforementioned embodiment.

With respect to an intake per day of the diet food of this embodiment, the amount of the ω-6 PUFA generally supplied to an adult over a treatment period is preferably 2.0 g or more. Also, the amount of the L-arginine, the L-ornithine or the mixture of them supplied to an adult over the treatment period is preferably 10 g or more.

The diet food or the supplement is administered preferably for 15 days or more, for example, over 15 through 60 days and once through four times a day.

Accordingly, the amount of the ω-6 PUFA included in the diet food ingested per day is preferably not less than 0.5 g and not more than 10 g, and the amount of the L-arginine or the L-ornithine is preferably not less than 3 g and not more than 40 g.

However, the amounts of the ω-6 PUFA and the L-arginine, the L-ornithine or the mixture of them to be supplied per day for attaining a desired effect can be varied depending upon the treatment period (days) and individual factors of a patient or the like to be treated.

The ω-6 PUFA may be included in the form of fish oil. In this case, when the pH is adjusted to approximately 3 through 4 by an edible acid, the smell peculiar to the fish oil can be reduced. Also, when the fish oil is encapsulated, the smell can be sealed and degradation of the fish oil through oxidation can be suppressed so as to improve the storage property.

The actions and effects of the L-arginine and the L-ornithine included in the diet food of this embodiment are the same as those described in Embodiment 1.

The ω-6 PUFA of this embodiment is bonded to freed glycerin so as to prevent the glycerin from re-converted into triglyceride and being stored in fat cells in the same manner as the ω-3 PUFA. Also, during the practice of the dieting system for obesity or an adult disease, the ω-6 PUFA advantageously affects resistance against catabolism, that is, a state where self-organization is combusted for generating energy.

When the L-arginine or the L-arginine precursor is added in this embodiment, the L-arginine or the like has not only an action to accelerate the secretion of the growth hormone for activating the metabolism but also an action to activate lipase, that is, a lipolytic enzyme in the same manner as in Embodiment 1.

On the other hand, when the L-ornithine or the L-ornithine precursor is added in this embodiment, the L-ornithine or the like affects the hypophysis of the taker so as to activate the synthesis and the release of the growth hormone and facilitate the metabolism of somatic cells, resulting in accelerating the decomposition and the consumption of the body fat.

Furthermore, the ω-6 PUFA included in the diet food of this embodiment is bonded to the glycerin freed from the neutral fat within the body of the taker. Thus, the ω-6 PUFA prevents the endogenous fatty acid from bonded into triglyceride again to be stored in the fat tissues. Moreover, since the ω-6 PUFA advantageously affects the resistance against the catabolism, the safety of the dieting can be improved.

As a result, the diet food of this embodiment effectively reduces the body fat of the taker through the synergistic effect of the ω-6 PUFA and the L-arginine or the L-ornithine, so as to prevent/improve adult diseases and obesity.

It is noted that ω-3 PUFA may be combined with the ω-6 PUFA to be additionally included in the diet food of this embodiment.

Embodiment 3

A diet food of this embodiment includes a mixture of at least one of diacylglycerol, middle or short chain fatty acid and phytosterol and at least one of L-arginine, L-ornithine, an L-arginine precursor and an L-ornithine precursor.

In this embodiment, the diacylglycrol is two molecules of fatty acid bonded to one molecule of glycerin and has a property that it is minimally re-synthesized into fat after being absorbed into a body.

Among medium or short chain fatty acids, those having a carbon number of 8 through 10 or not more than 8 have a higher water-soluble property than a general long chain fatty acid and are easily combusted.

The phytosterol has a property to dissolve in bile acid and has a function to reduce the absorption of general cholesterol.

The actions and effects of the L-arginine, the L-ornithine, the L-arginine precursor and the L-ornithine precursor of this embodiment are the same as those described in each of the above-described embodiments.

According to the diet food of this embodiment, owing to the synergistic effect of the diacylglycerol, the medium or short chain fatty acid or the phytosterol and the L-arginine or the L-ornithine, body fat can be safely and effectively reduced, so as to prevent/improve an adult disease or obesity.

Alternative Embodiments

In an alternative embodiment of this invention, the diet food may include at least one of nucleo-bases, nucleosides and nucleic acids.

The nucleo-bases are preferably at least one of adenine, guacine, hypoxanthine, xanthine, cytosine, uracil and thymine.

The nucleosides are preferably at least one of uridine, adenosine, guanosine, cytidine, ribothymidine, deoxyadenosine, deoxyguanosine, deoxyuridine, deoxycytidine, thymidine, inosine and xanthosine.

The nucleic acids are preferably at least one of DNA, RNA and polynucleotide obtained by polymerizing nucleotides. As a purified nucleic acid substrate source, for example, baker's or brewer's yeast RNA or fish seed DNA is preferred. However, another source such as meat may be used as a starting source.

The nucleo-bases, the nucleosides and the nucleic acids have an action to increase energy consumption required in intracellular metabolism in a process mainly from RNA assembly to protein synthesis. Accordingly, energy generated through combustion of free fatty acid that is inhibited from re-bonding to glycerin is effectively consumed in the process from the RNA assembly through recruit of amino acid to the synthesis of peptide and protein. Therefore, the nucleo-bases, the nucleosides and the nucleic acids work to reinforce the fat metabolizing action of the diet food of this invention.

Alternatively, the diet food may include nucleotides. The nucleotides include phosphate esters of natural nucleosides, for example, monophosphate esters such as adenylate (AMP), guanilate (GMP), uridilate (UMP), cytidilate (CMP), deoxythymidilate (dTMP) and deoxycytidilate (dCMP), and diphosphate esters or triphosphate esters of natural nucleoside such as ADP and ATP.

A dose of the nucleic acid substrate source is varied depending upon the type of a desired treatment, the condition of a patient to be treated and the like. For example, when the patient to be treated is an adult, 0.1 through 4.0 g, preferably 1.0 through 3.0 g and most preferably 1.25 through 2.5 g of RNA or an equivalent weight of another nuclear substrate is set as a dose per day. When the diet food of this invention thus including a given amount of nucleic acids is used, an effective response of salvage nucleic acid synthesis can be easily obtained. In this invention, one weight unit of nucleic acid substrate is regarded to be equal to 2.5 through 3.0 weight units of RNA, DNA, a nucleoside or a nucleotide.

In another embodiment, the diet food may include at least one of maltodextrin, cluster dextrin and indigestible dextrin.

In this embodiment, the maltodextrin, the cluster dextrin and the indigestible dextrin included in the diet food is obtained by reducing the molecular weight of starch by a chemical or enzymatic method.

These dextrin can supplement energy of the diet food in an idealistic manner. Specifically, when such dextrin is ingested, the blood sugar level is more moderately increased than when glucose, sucrose or fructose is ingested. Therefore, the secretion of insulin into the blood is not excessive, and various intracellular signal transduction systems are not excessively activated, resulting in suppressing an unreasonable biological reaction related to acceleration of obesity or arterial sclerosis arising from excessive change of the blood sugar. Accordingly, the taker is free from abrupt hunger or fatigue even when he/she is on a diet.

Furthermore, for adjusting the taste, a low-calorie sweetener such as aspartyl phenylalanine methyl ester (brand name: Aspartame) may be included.

In another embodiment, the diet food may include a water-absorbing fiber component. Soluble fiber of this embodiment means fiber that can substantially fermented mainly in a colic so as to produce short chain fatty acid. Preferable examples of the soluble fiber are pectin, guar gum, locust bean gum and xanthan gum. Such soluble fiber is hydrated and swells in the gastrointestinal tract, so as to provide physical and psychological satiety to the taker. Also, such a substance has an action to suppress absorption into the body of lipid and carbohydrate and hence reinforces the effects of the diet food.

A dose per day of the soluble fiber of this embodiment is approximately 3.0 through 30 g per day for an adult.

In another embodiment, the diet food may include mucopolysaccharides. Preferable examples of the mucopolysaccharides are hyaluronic acid, chondroitin, chondroitin sulfate, dermatan sulfate and heparin.

In another embodiment, the diet food may include an anorectic component.

As a preferable anorectic component, an appropriate amount of a substance for suppressing uptake of serotonin, that is, a hormone for accelerating the intestinal movement, such as fluoxetine, or an alkaloid is effectively included.

In another embodiment, the diet food may include a component having an absorption suppressing action for saccharide and lipid. Preferable examples of the absorption suppressing component are yohimbine that suppresses decomposition of lipid, a glucosidase inhibitor having a carbohydrate absorption inhibiting action, *Aralia elata* of Alariaceae, gymnema extract, chitin chitosan, sylvestre and polyphenol. These substances are useful for reinforcing the effects of the diet food of this invention.

In another embodiment, the diet food may include yoghourt or a probiotics material derived from yoghourt.

The yoghourt or the probiotics material derived from yoghourt included in the diet food is useful for keeping the health of a person who is on a diet by using the diet food. The probiotics material means living microbes with properties useful for the health of humans, and polyamines, that is, the product of the probiotics material, are known to accelerate the cell protein synthesis and to have the breeding activity. Owing to the actions of the polyamines, it is easy to continuously practice the dieting while retaining the body functions.

In this embodiment, the probiotics material is sealed within a capsule or appropriately processed by, for example, pulverizing through freeze-drying to be added to the diet food. Also, the diet food may be ingested in a combination with yoghourt or the like.

In this invention, the diet food may include at least one of glutamine, vitamin A, vitamin C, vitamin D, vitamin E, vitamin K, folic acid, thiamine, riboflavine, vitamin B6, vitamin B12, niacin, biotin, pantothenic acid, β-carotene, linolenic acid, triglyceride linolenate, triglyceride eicosapentaenate and triglyceride docosahexaenate.

The diet food can further include mineral elements or minor elements, in a pharmacologically allowable form, such as sodium, potassium, calcium, phosphorus, magnesium, manganese, copper, zinc, iron, selenium, selenium chloride, chromium and molybdenum.

In this invention, the active ingredients of the diet food are preferably substances derived from natural products.

The diet food of this invention not only exhibits the function to improve obesity or an adult disease diathesis but also keeps a person under calorie control resistant to the catabolism, and therefore, it is suggested to be useful for improving cibophobia.

The invention will now be described by the following examples:

Example 1

A sixty-five-year-old female (with a height of 156 cm, a weight of 85 Kg and a blood pressure of 176/104 mmHg) was made to ingest the diet food of this invention having the compositions listed in FIG. 1 for three weeks instead of lunch out of general breakfast, lunch and supper. In this example, the diet food was in a liquid form and the intake per meal was 250 ml. It is noted that the other meals were not controlled at all.

As a result, the weight of this person was reduced by approximately 3.5 Kg and the blood pressure was lowered to 154/88 mmHg, and she felt dull headache became improved and her body lighter as the subjective signs.

Example 2

Also, a fifty-one-year-old male (with a height of 167 cm and a weight of 69 Kg) was made to ingest the diet food of this invention having the compositions listed in FIG. 1 for eight weeks instead of lunch out of general breakfast, lunch and supper. In this example, the diet food was in a liquid form and the intake per meal was 250 ml. It is noted that the other meals were not controlled at all.

As a result, the weight of the male was reduced by approximately 2 Kg in 30 days and by 3 Kg in 60 days as compared with that weighed before the dieting.

Furthermore, the male subject was made to ingest the diet food instead of breakfast and lunch out of general breakfast, lunch and supper twice a day at 8 a.m. and noon.

As a result, the weight was further reduced by approximately 2 Kg in 30 days. Accordingly, over the whole dieting period, the supper was not controlled at all and there was no restriction in snacks and night snacks, but the weight loss of 5 Kg in total in 90 days was achieved without causing any symptom of malaise or other complications.

Example 3

A forty-nine-year-old male having hypertension, diabetes and adiposis (with a height of 169 cm, a weight of 106.2 Kg, a blood pressure of 144/93 mmHg with medication and fasting blood sugar of 145 mg/ml) was made to ingest the diet food of this invention having the compositions listed in FIG. 1 for two weeks as lunch in combination with calorie-controlled meals of 450 kcal for breakfast and 510 kcal for supper. In this example, the diet food was in a liquid form, and the intake per meal was 250 ml.

As a result, after two weeks, the weight was reduced to 99.8 Kg, the blood pressure was lowered to 115/79 mmHg and the fasting blood sugar was lowered to 95 mg/ml, and thus, all the measurement items were remarkably improved. Furthermore, four weeks after, the weight was reduced to 96.7 Kg, the blood pressure was lowered to 104/74 mmHg and the blood sugar was lowered to 79 mg/ml.

On the other hand, the serum protein was lowered from 6.7 g/dl to 6.1 through 6.0 g/dl once but was increased to 6.5 g/dl after four weeks. The serum albumin was also lowered from 3.7 g/dl to 3.5 through 3.4 g/dl once but was increased to be higher than the initial value to 3.8 g/dl after four weeks. The cholesterol was lowered from 165 mg/dl to 150 through 143 mg/dl once but was increased to 162 mg/dl after four weeks.

These data reveal that the present diet food can reduce a weight without causing any reluctance, hunger or malaise and is a good health food capable of reducing adult disease dispositions including hypertension, diabetes and hyperlipemia.

INDUSTRIAL APPLICABILITY

As described so far, the diet food of this invention is useful for preventing or improving obesity or adult, life-style related, diseases such as diabetes, hypertension, and hyperlipemia.

The invention claimed is:

1. A method for reducing weight in a subject in need thereof comprising administering to said subject an effective amount of a composition consisting of:
   at least one of omega-3 polyunsaturated fatty acid (PUFA) or a combination of omega-3 PUFA and omega-6 PUFA;
   at least one of L-arginine, L-ornithine, an L-arginine precursor or an L-ornithine precursor; and
   at least one of a nucleobase, a nucleoside or a nucleic acid.

2. The method according to claim 1, wherein for one serving of the composition:
   0.1-3.5 g of omega-3 PUFA are administered; and 0.6-15 g of at least one of L-arginine, L-ornithine, an L-arginine precursor or an L-ornithine precursor are administered.

3. The method according to claim 1, wherein the nucleobase is at least one of adenine, guacine, hypoxanthine, xanthine, cytosine, uracil or thymine.

4. The method according to claim 1, wherein the nucleoside is at least one of uridine, adenosine, guanosine, cytidine, ribothymidine, deoxyadenosine, deoxyguanosine, deoxyuridine, deoxycytidine, thymidine, inosine or xanthosine.

5. The method according to claim 1, wherein the nucleic acid is at least one of DNA, RNA or polynucleotide obtained by polymerizing nucleotides.

6. The method according to claim 1, wherein for one serving of the composition there is 0.1-1.5 g of at least one of a nucleobase, a nucleoside or a nucleic acid.

7. The method according to claim 1, wherein the composition is derived from natural products.

8. The method according to claim 1, wherein the composition consists of:
   0.02-1.2 wt % of omega-3 PUFA;
   0.1-6 wt % of at least one of L-arginine, L-ornithine, an L-arginine precursor or an L-ornithine precursor; and
   0.02-2 wt % of nucleic acid.

9. The method according to claim 1, wherein the subject is a domestic animal, a fowl or a pet.

10. A method for treating obesity, hyperlipidemia and/or hypertension in a subject suffering from obesity, hyperlipidemia and/or hypertension comprising administering to said subject an effective amount of a composition consisting of:
   omega-3 polyunsaturated fatty acid (PUFA);
   at least one of L-arginine, L-ornithine, an L-arginine precursor or an L-ornithine precursor; and
   at least one of a nucleobase, a nucleoside or a nucleic acid.

* * * * *